(12) United States Patent
Mentzen et al.

(10) Patent No.: US 6,613,542 B2
(45) Date of Patent: Sep. 2, 2003

(54) TESTING SYSTEM FOR CHEMICAL SUBSTANCES OR SUBSTANCE MIXTURES

(75) Inventors: Jörg Mentzen, Geita (TZ); Helmut Kessmann, Lörrach (DE); Harald Danigel, Basel (CH); Gerhard Klokow, Rheinfelden-Herten (DE); Peter Obergfell, Freiburg (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 8 days.

(21) Appl. No.: 09/881,072

(22) Filed: Jun. 14, 2001

(65) Prior Publication Data

US 2002/0110920 A1 Aug. 15, 2002

Related U.S. Application Data

(62) Division of application No. 09/117,968, filed as application No. PCT/EP97/00985 on Feb. 28, 1997, now Pat. No. 6,277,642.

(30) Foreign Application Priority Data

Mar. 5, 1996 (DE) ............................................ 96810124

(51) Int. Cl.[7] .............................. C12Q 1/02; C12Q 1/00
(52) U.S. Cl. ....................... 435/29; 435/4; 435/283.1; 436/54; 436/174; 436/180
(58) Field of Search ........................... 435/29, 4, 283.1; 436/54, 174, 180

(56) References Cited

U.S. PATENT DOCUMENTS 6,277,642 B1 * 8/2001 Mentzen et al. ............... 436/54

* cited by examiner

Primary Examiner—Louise N. Leary
(74) Attorney, Agent, or Firm—William A. Teoli, Jr.; Thomas Hamilton

(57) ABSTRACT

In a testing system for chemical substances or substance mixtures, especially for potential plant protection compositions, the chemical substance to be tested or the substance mixture to be tested is applied to a test specimen, especially to plants or parts of plants. When a predetermined period of time has elapsed, the test specimen is examined for the activity of the substance or substance mixture. For this purpose, first of all a type of test specimen is selected from a stock of test specimens, and the substances to be tested are selected from a stock of substances to be tested. The selected type of test specimen and the selected substances are identified (BC1, BC2) by means of a machine-readable code and those codes are supplied to a memory unit (12). The test specimens are placed in readiness in a carrier plate (30), for which purpose each test specimen or a section (BR) of test specimen is deposited in a well (300) that is provided in the carrier plate (30) and that is partly filled with a nutrient solution (301). Then a spraying device (150, 151) is inserted into the well (300) of the carrier plate (30) and sprays the test specimen deposited therein with the selected substance and is then removed from the well (300) again or the spraying device is positioned immediately above the well (300) of the carrier plate (30) and sprays the test specimen deposited therein with the selected substance.

7 Claims, 7 Drawing Sheets

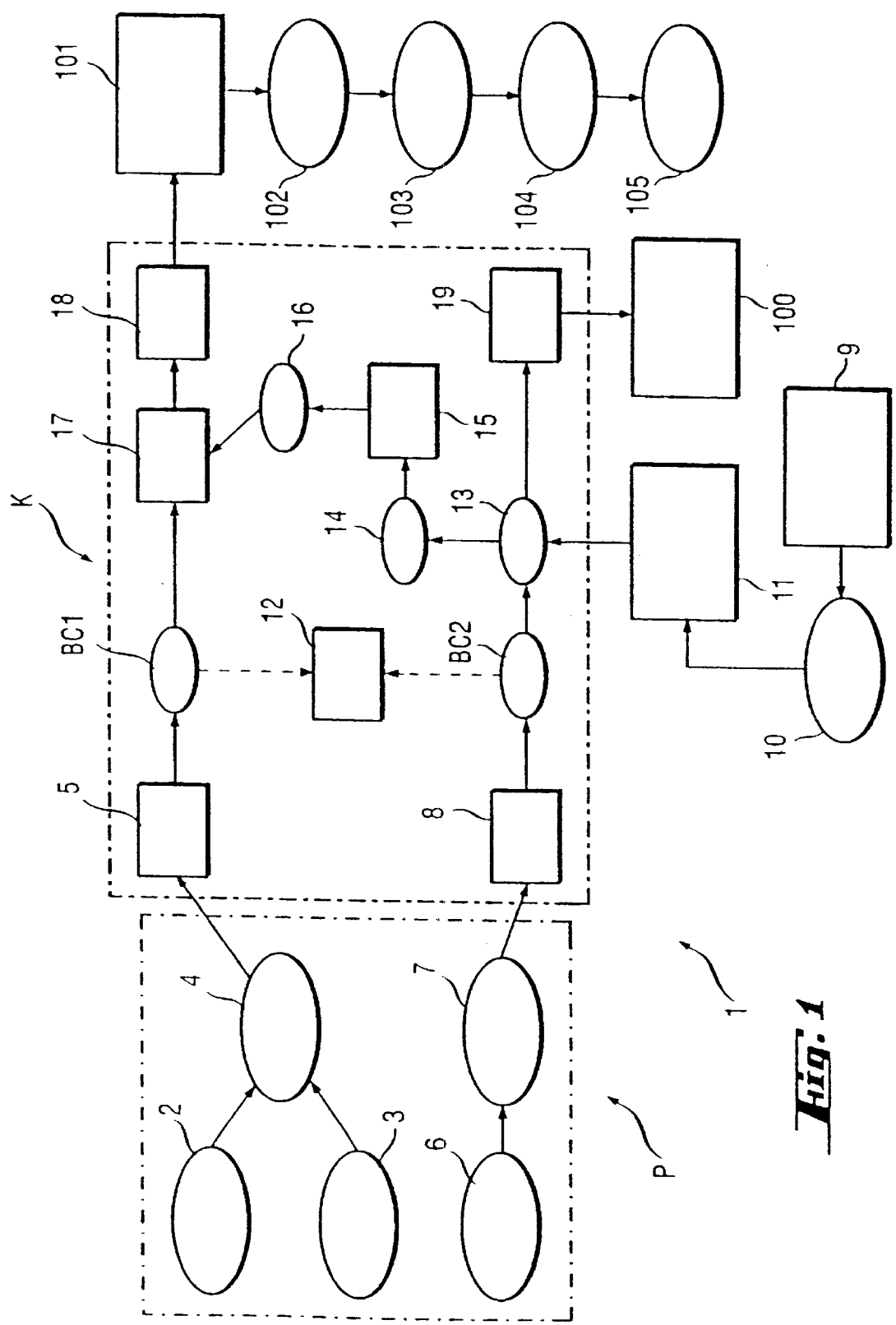

Figure 4:
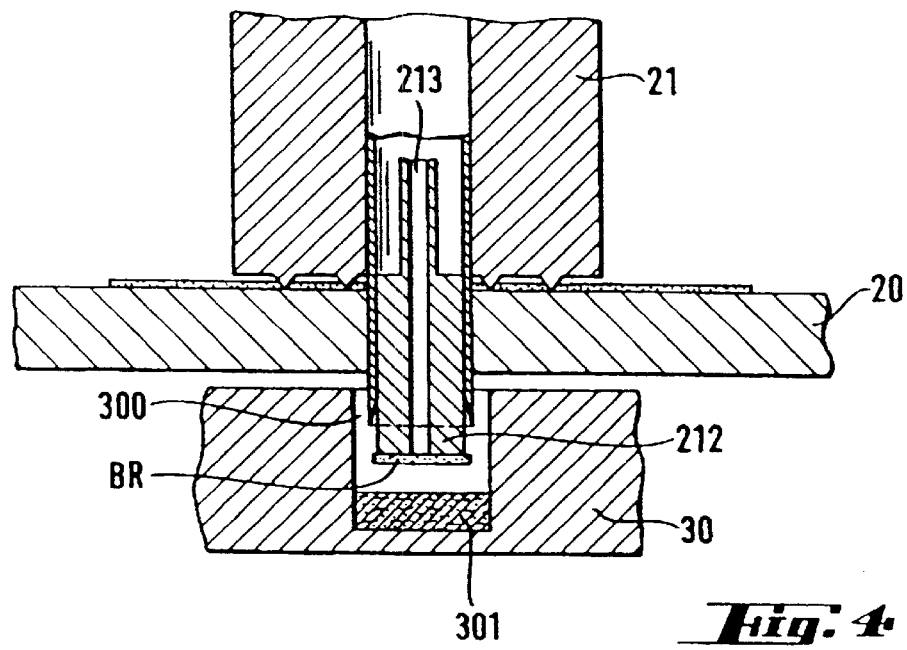

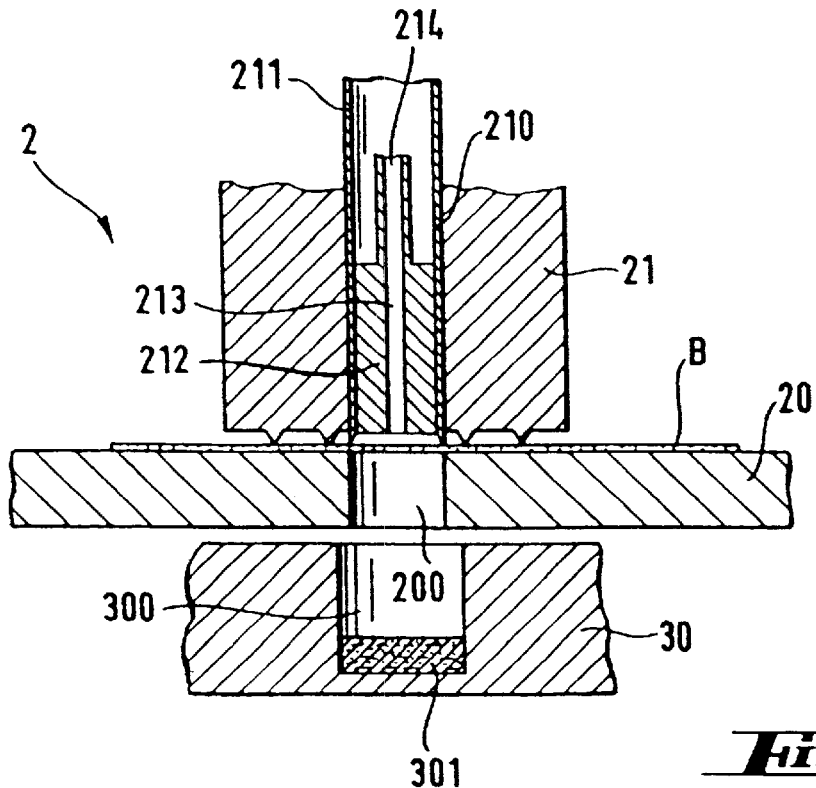
Fig: 2
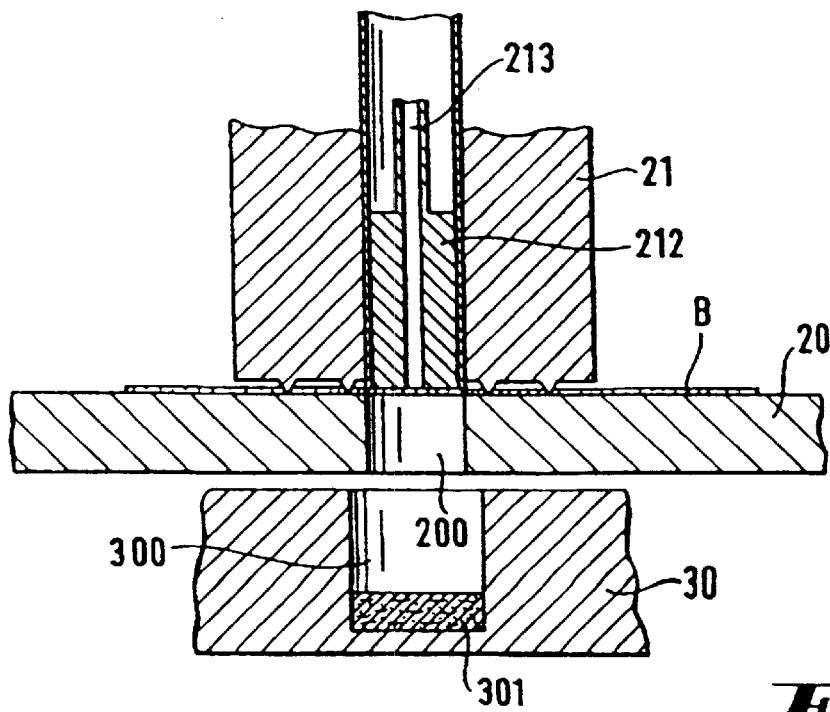
Fig: 3

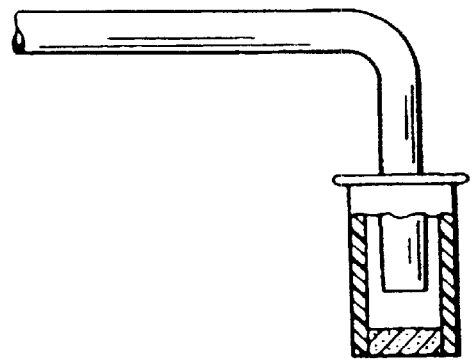
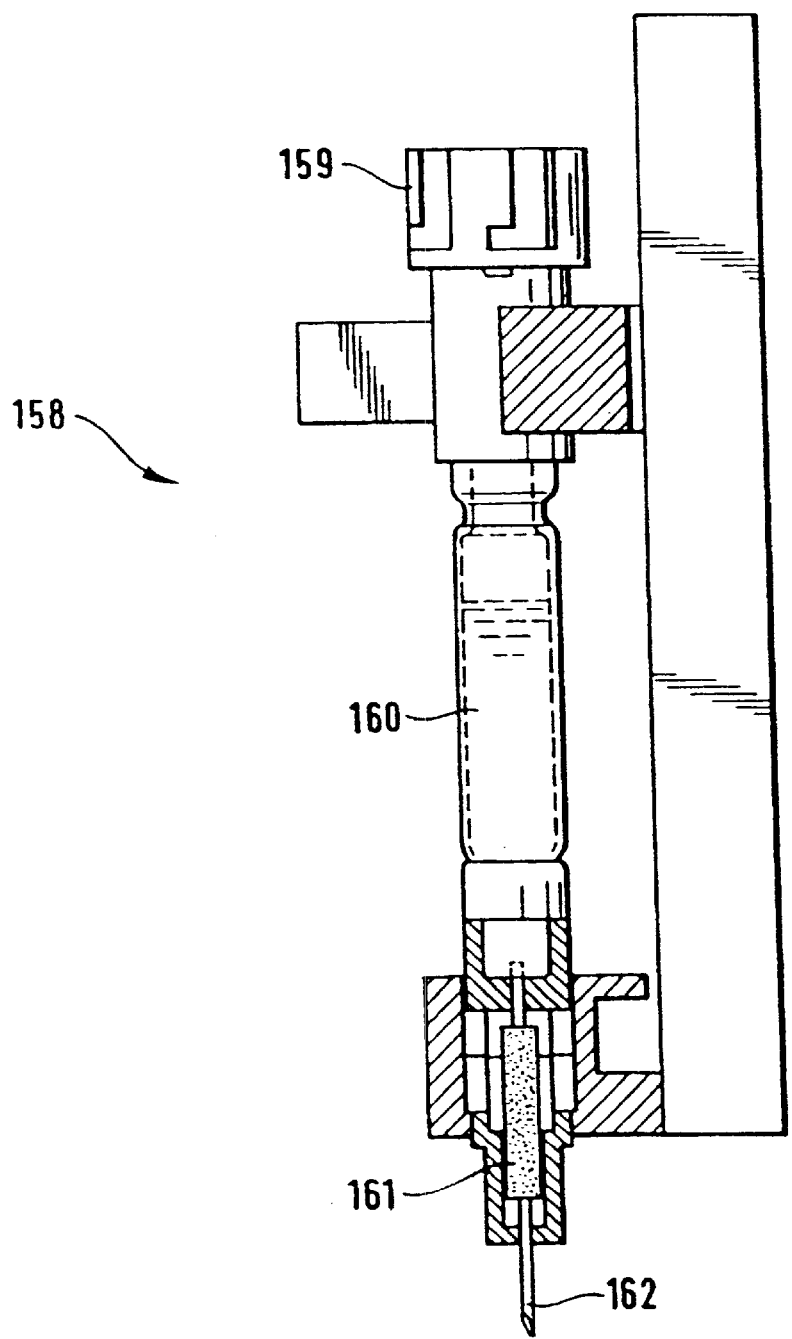
Fig. 8

TESTING SYSTEM FOR CHEMICAL SUBSTANCES OR SUBSTANCE MIXTURES

This application is a division of Ser. No. 09/117,968, filed Feb. 16, 1999, now U.S. Pat. No. 6,277,642, which is a national stage entry of PCT/EP 97/00985, filed Feb. 28, 1997.

The invention relates to a testing system for chemical substances or substance mixtures and to a method of testing chemical substances or substance mixtures for their activity, especially for testing potential plant protection compositions, such as insecticides, fungicides, herbicides and the like.

WO 86/04919 discloses a method for the in vitro culturing of plant cells which comprises applying freely movable buoyant bodies to the surface of the liquid nutrient medium and culturing the plant constituents on the surface of those buoyant bodies. Also disclosed is a culturing vessel having additional devices for the supply and removal of liquids or gases, for the circulation thereof in the vessel and for the regulation of physical and chemical variables.

EP-A-0 323 205 describes a device for the application of herbicides by means of a rod-shaped arrangement on which spray nozzles are mounted.

The testing of chemical substances or substance mixtures (for the sake of simplicity reference is made always to one substance hereinafter) for their activity, especially the testing of potential plant protection compositions (pesticides), such as insecticides, a fungicides, herbicides, nematicides, acaricides and the like, is nowadays generally carried out by bringing plants or parts of plants, for example sections of leaves, into contact with the substance to be tested. Where the aim of the test is merely to discover whether or not the substance as such is able to cause damage to the leaf section (for example in the case of a herbicide) there is no need for the leaf section to be infested with a pest, a fungus or the like; otherwise the leaf section needs also to be infested with the appropriate pest, fungus or the like (for example when the substance is a fungicide or insecticide). After some time the leaf section is examined for the activity of the substance applied.

As a rule, the substance to be tested is applied to the leaf section manually using a pipette or in the case of entire plants is generally sprayed on. Since the number of substances which it is desirable to test for activity is very large and is steadily and rapidly increasing, the manual application of the individual substances using a pipette, although possible in principle, has only a limited degree of suitability because it is very complicated and time-consuming, so that the steadily increasing number of substances which it is desirable to test for activity cannot be managed in this way in practice and requires the constant employment of qualified personnel. Moreover, it is also difficult to wet the test specimen (e.g. leaf sections, comminuted parts of plants, seeds or entire plants) evenly with the substance to be tested, so that it is hard to obtain reliable information about the activity of a substance. If a number of test specimens, arranged one next to the other, are sprayed with different substances there is also a risk that a neighbouring test specimen will become contaminated, so that thereafter the action of the substance tested on the neighbouring test specimen may affect or even completely falsify the result.

An aim of the invention is therefore to provide a method of testing pesticides and a testing system for carrying out that method which does not have the disadvantages mentioned above and which therefore allows, especially, a high throughput of substances to be tested and specimens to be tested, while at the same time allowing reliable identification and categorisation of the test specimens and of the substances tested, in which, furthermore, contamination of neighbouring test specimens is ruled out and which is automated to the highest possible degree, so that it is particularly efficient, that is to say, for example, it is also able to operate overnight and without supervision.

That problem is solved by the method according to the invention and by its testing system. According to the invention there is therefore proposed a method of testing pesticides for their activity, wherein the pesticide to be tested is applied to a test specimen, especially to plants or parts of plants, such as sections of leaves and the like, and, after a predetermined period of time has elapsed, the test specimen is examined for the activity of the pesticide, in which method first of all a type of test specimen is selected from a stock of test specimens, and the pesticides to be tested are selected from a stock of pesticides to be tested; the selected type of test specimen and the selected pesticides are then identified (BC1, BC2) by means of a machine-readable code and those codes are supplied to a memory unit (12), the test specimens being placed in readiness in a carrier plate (30) by deposition of each test specimen or a section (BR) of test specimen in a well (300) that is provided in the carrier plate (30) and is at least partly filled with a nutrient solution (301) or a gel and the carrier plate being thus charged; and then either a spraying device (150, 151, 158) is positioned immediately above the well(s) (300) of the carrier plate (30) and sprays the test specimen deposited therein with the pesticide, or the spraying device (150, 151, 158) is inserted into the well(s) (300) of the carrier plate (30) and sprays the test specimen deposited therein with the selected pesticide and is then removed from the well (300) again.

Preferably the pesticides are herbicides, fungicides or insecticides.

Preference is given to a method wherein first of all a type of test specimen is selected from a stock of test specimens, and the substances to be tested or the substance mixtures to be tested are selected from a stock of substances or substance mixtures to be tested; the selected type of test specimen and the selected substances or the selected substance mixtures are then identified (BC1, BC2) by means of a machine-readable code and those codes are supplied to a memory unit (12), the test specimens being placed in readiness in a carrier plate (30) by deposition of each test specimen or a section (BR) of test specimen in a well (300) that is provided in the carrier plate (30) and is at least partly filled with a nutrient solution (301) or a gel and the carrier plate being thus charged; and then a spraying device (150, 151, 158) is inserted into the well(s) (300) of the carrier plate (30) and sprays the test specimen deposited therein with the selected substance or the selected substance mixture and is then removed from the well (300) again.

Preference is given also to a method wherein first of all a type of test specimen, e.g. a specific plant variety, is selected from a stock of test specimens, and the substances to be tested or the substance mixtures to be tested are selected from a stock of substances or substance mixtures to be tested; the selected type of test specimen and the selected substances or the selected substance mixtures are then identified (BC1, BC2) by means of a machine-readable code and those codes are supplied to a memory unit (12), the test specimens being placed in readiness in a carrier plate (30) by deposition of each test specimen or a section (BR) of test specimen in a well (300) that is provided in the carrier plate (30) and is at least partly filled with a nutrient solution (301) or a gel and the carrier plate being thus charged; and then a spraying device (150, 151, 158) is positioned immediately above the well(s) (300) of the carrier plate (30) and sprays the test specimen deposited therein with the selected substance or the selected substance mixture.

In an especially preferred embodiment of the method according to the invention the test specimen is first conveyed to a stamping device (2) which automatically stamps out a section, for example a leaf roundel (BR), from the test specimen, retains the stamped-out section after it has been stamped out and then deposits it in a well (300) in the carrier plate (30) that is at least partly filled with nutrient solution (301) or a gel.

More especially preferred is an embodiment wherein a plurality of substance concentrates or substance mixture concentrates, each is of which has been deposited in wells in a plate, are placed in readiness in a second inlet storage means (8), and a mixing device (13) is provided for the preparation of the substance to be applied to the test specimen, or of the substance mixture to be applied to the test specimen, from the concentrate present in the well in question and an auxiliary mixture (11), and the substance so prepared or the substance mixture so prepared is then conveyed to the spraying device (150, 151, 158).

The test specimen is especially an entire plant.

The testing system according to the invention for carrying out the method comprises a first inlet storage means (5) in which a large number of carrier plates (30) charged with test specimens is stored temporarily before spraying.

Preference is given to a testing system wherein the spraying device comprises a nozzle body (150) having a sealing ring (152) which is so arranged that, on insertion of the nozzle(s) (151) of the nozzle body (150) into the respective well (300) of the carrier plate. (30), the sealing ring tightly surrounds the well (300) in the carrier plate (30), and the spraying device has a reservoir (156) for the substance to be applied to the test specimen or the substance mixture to be applied to the test specimen and a spray channel (153) which is provided with a compressed air connection at its end remote from the test specimen, the reservoir (156) and the spray channel (153) being connected to one another by a very narrow feed channel (157) which opens into the spray channel (153).

Special preference is given to a testing system wherein the spraying device comprises one or more micropipettes (158), each of which has a stock container (160) into which the substance or substance mixture is first introduced by suction, and then, using a piezoelectric droplet generator, one or more droplets of a well defined size are expelled through a nozzle (162) at a well defined rate and the test specimen is thus sprayed.

Special mention should also be made of an embodiment of the testing system wherein the nozzle body (150) has a plurality of linearly arranged nozzles and associated reservoirs and also spray and feed channels and sealing rings or a plurality of linearly arranged micropipettes (158), the distance (D) between the individual nozzles or micropipettes corresponding to the distance (E) between the wells (300) within a line of the carrier plate (30).

Especially preferred is a testing system wherein the nozzle body (150) comprises an air inlet channel (154) or channels and an air outlet channel (155) or channels, which are each so arranged that while the nozzle (151) is inserted in the respective well (300) of the carrier plate (30) the channels are in communication with the well (300).

The testing system according to the invention is especially suitable for testing insecticides, fungicides, herbicides, acaricides or nematicides, more especially insecticides, fungicides or herbicides.

The testing system according to the invention allows especially the testing of a very large number of substances and test specimens and reliable identification and categorisation of the test specimens and of the substances tested. Furthermore, contamination of neighbouring test specimens is reliably avoided and therefore the result of the test is not affected or falsified. Moreover, the testing system according to the invention enables operation to be, fully automatic to a greater or lesser extent, especially overnight and without supervision. The dependent patent claims relate to especially advantageous configurations of the testing system.

Figure 5:
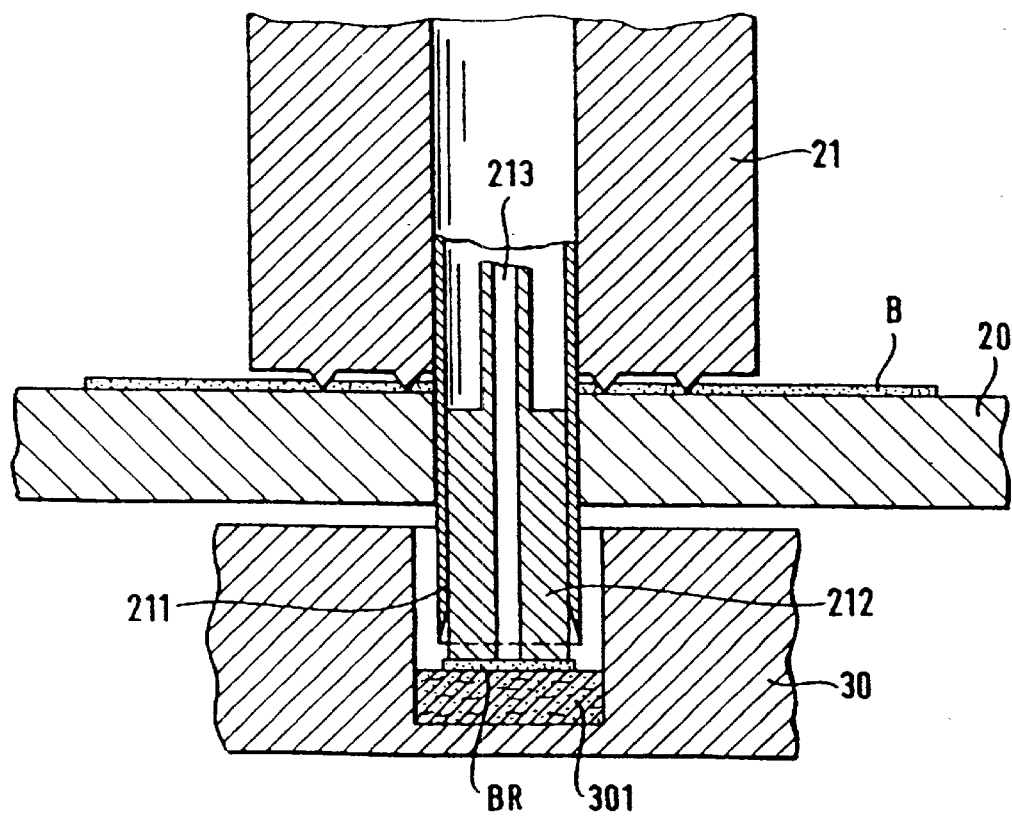
Figure 6:
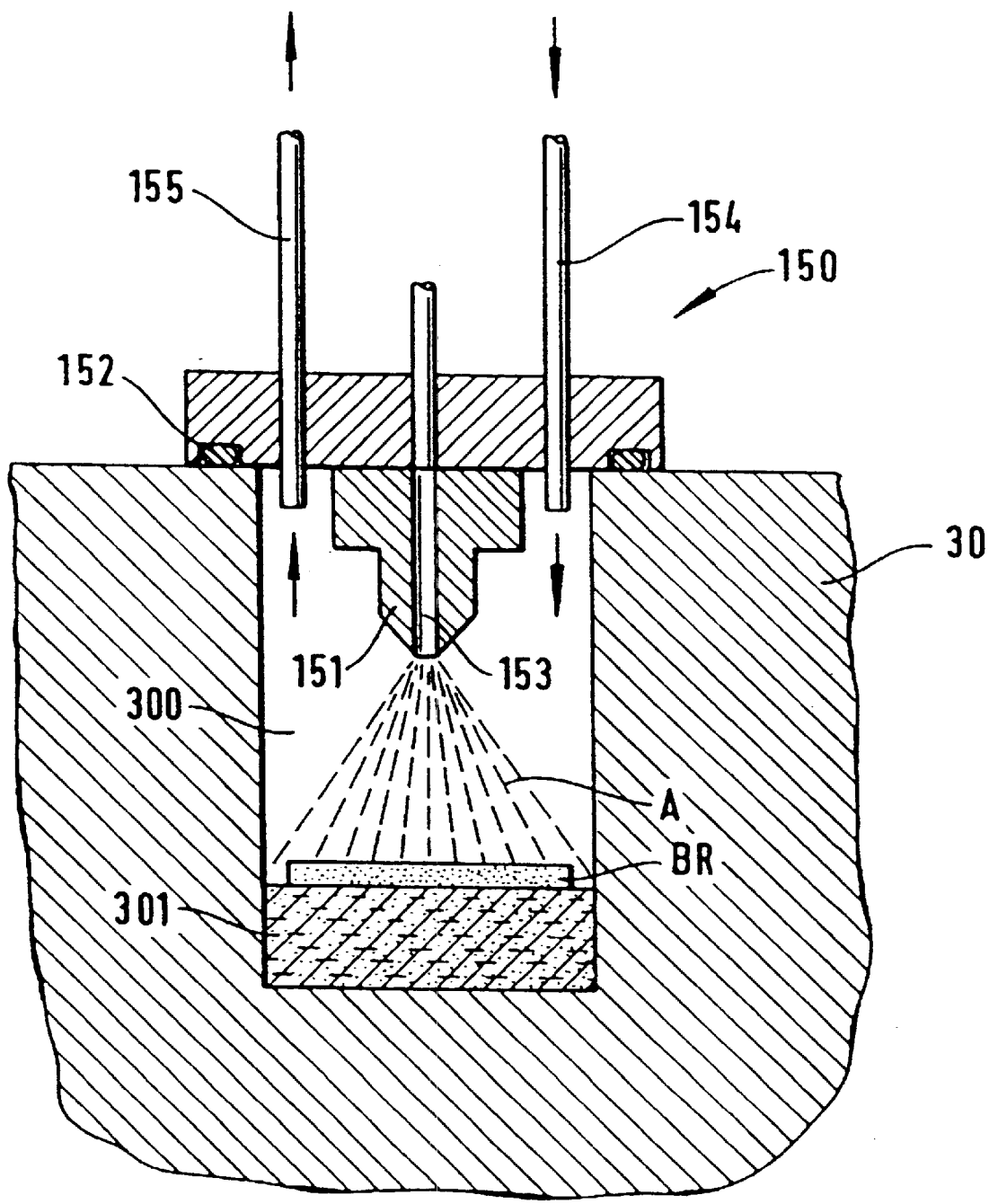
Figure 7:
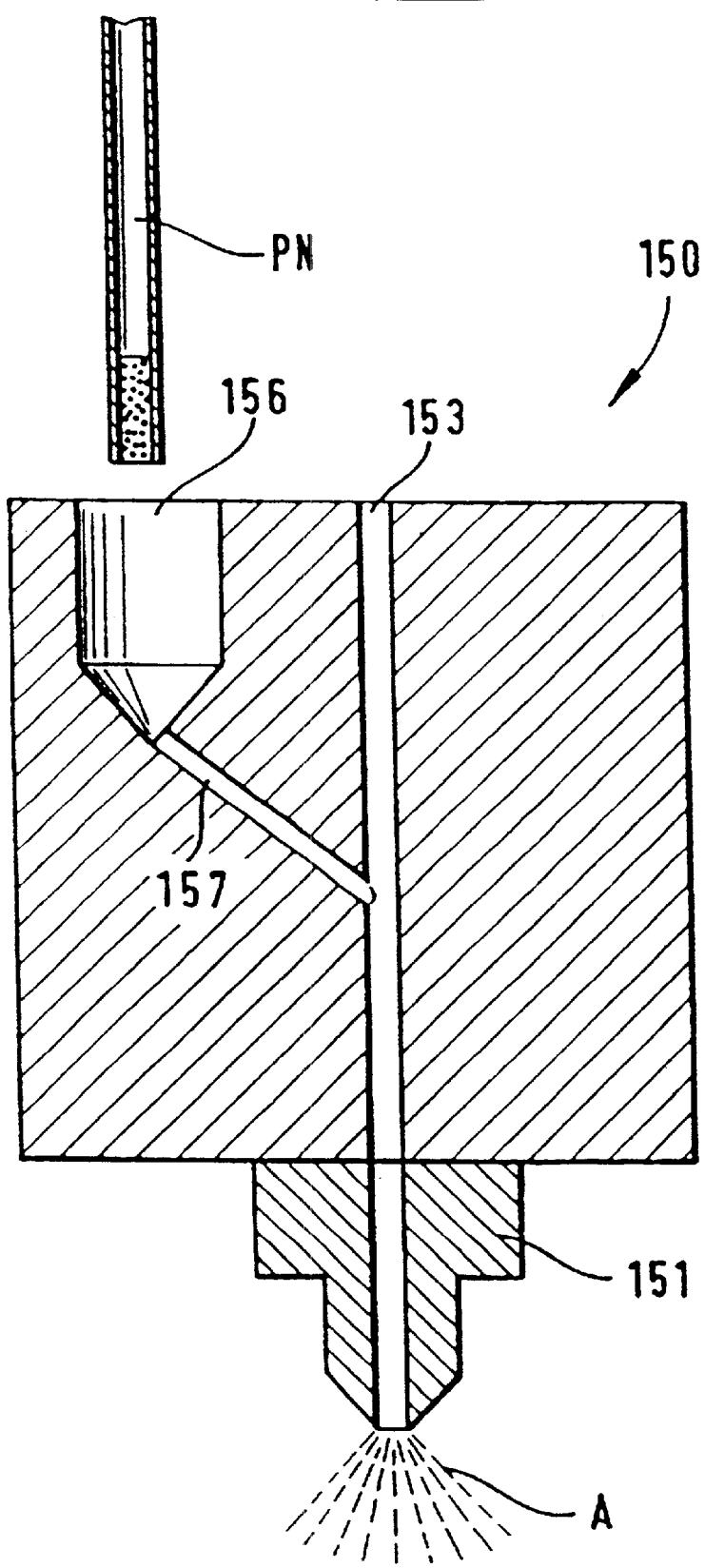
Figure 9:
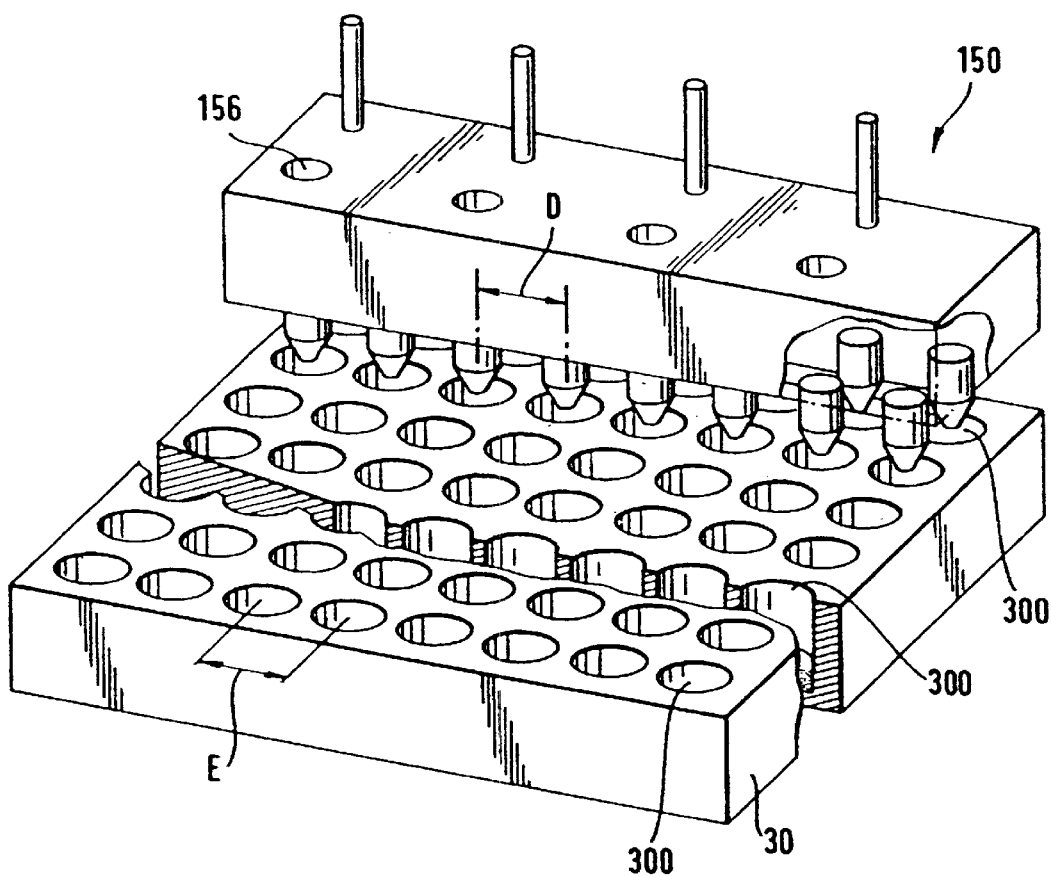

The invention will be described in greater detail below with reference to the drawings, which are partly diagrammatic and/or in section:

FIG. 1 is a block diagram of an embodiment of the testing system according to the invention having functional blocks to illustrate in principle the mode of operation of the testing system, FIG. 2 shows an embodiment of the stamping device of the testing system according to the invention shortly before the start of the stamping operation, FIG. 3 shows the stamping device of FIG. 2 during the cutting operation, FIG. 4 shows the stamping device of FIG. 2 with a stamped-out section of a leaf, shortly before the leaf is deposited in a well in a carrier plate, FIG. 5 shows the stamping device of FIG. 2 during deposition of the stamped-out leaf section, FIG. 6 shows a portion of an embodiment of the spraying device of the testing system according to the invention, in which the nozzle is inserted in the well in the carrier plate and the spraying device seals the well, FIG. 7 shows a portion of the nozzle body in detail, FIG. 8 is a further embodiment of the spraying device of the testing system according to the invention (micropipette), and FIG. 9 shows an embodiment of a nozzle body in which the individual nozzles are arranged in a line and above corresponding wells in a carrier plate.

The block diagram in FIG. 1 shows an embodiment of the testing system according to the invention, in which the individual functional blocks need not all be realised separately in physical terms; the block diagram is primarily intended to give an overview of the mode of operation of the testing system according to the invention. Individual components of the testing system will be explained in detail below.

The embodiment of the testing system shown in FIG. 1 and indicated as a whole by the reference numeral 1 is basically divided into two fundamental zones—a peripheral zone P, in which an operator still has scope for manual intervention, and a core zone K, in which the operator has no scope for intervention during operation, that is to say in which all operations take place fully automatically. This division into a peripheral zone P and a core zone K is explained in a little more detail below with reference to the individual operations that take place in the individual zones; it is an especially practical division, but such a division is not absolutely necessary for the fundamental mode of operation. Some other manner of division may be appropriate, depending upon the field of use.

In the peripheral zone P, a leaf roundel is stamped out from a leaf in a stamping device 2 (or alternatively a plurality of leaf roundels are stamped out simultaneously) and then deposited in a well in a carrier plate, for example a microtitre plate. The manner in which the stamping-out can be carried out will be explained in greater detail with reference to FIGS. 2 to 6. In order that the deposited leaf roundel receives a sufficient supply of nutrients the individual wells of the microtitre plates are filled with a nutrient solution, which may have been thickened to form a gel, for example using an algal extract generally known as agar. The leaf roundel is deposited in the well so filled. Since the nutrient solution or the gel is not liquid at room temperature, for the operation of filling the individual wells in accordance with Step 3 in FIG. 1, heating takes place prior to filling so that the state of aggregation is liquid for a short time for the purpose of filling the wells. The microtitre plate charged in this manner is then conveyed in a Step 4 to a first input storage means 5, which in this instance is part of the core zone K of the testing system 1.

The purpose of the first input storage means 5 is especially to ensure that there is always a sufficient number of charged microtitre plates (carrier plates) available so that operation in the core zone is continuous and the testing system is therefore utilised efficiently. It also means that, for example, in the evening charged microtitre plates are conveyed to the first input storage means 5 in sufficient numbers for operation in the core zone K of the testing system to take place fully automatically overnight and without supervision. The individual charged microtitre plates are provided with a machine-readable code. In this instance the bar-code represents, for example, a continuous numbering of the individual microtitre plates; it is therefore possible to use simple bar-code labels having serial numbering and it is not necessary to produce a special label for each microtitre plate. A data bank (not shown, for example an ORACLE data bank) then stores corresponding information as to which type of test specimen is located in the microtitre plate having which serial number. It will generally be the case (but is not necessarily so) that only one type of test specimen is present in the wells of the same microtitre plate. The information stored in the data bank therefore allows clear coordination between the bar-code being read and the type of test specimen.

In its core zone K the testing system 1, in addition to having the first input storage means 5 for the test specimens, also has a second input storage means 8. The second input storage means 8 is supplied with substance concentrates that, in a Step 6, are delivered in a container suitable for mechanical handling, e.g. a deep well plate (DWP) or, depending upon the amount of substance, a microtitre plate (MTP). The deep well plate conveyed to the core zone K is referred to as a "daughter plate" hereinafter. As a rule, however, the substance concentrates delivered in the daughter plates by the logistics system (these may be active substances dissolved in a solvent, e.g. dimethyl sulfoxide (abbreviated to DMSO below), acetone or N,N-dimethylformamide or mixtures thereof, preferably DMSO) will not be sprayed in the highly concentrated form onto the leaf roundels placed in readiness in the wells of the carrier plates, but rather it is preferable that the substance concentrate in question be processed by the mixing in of formulation auxiliaries, such as surfactants and also water, to form a suitable spray mixture—the spray mixture is then the substance actually to be sprayed onto the leaf roundel (and is hence the substance to be tested).

The preparation of the daughter plates is carried out in the logistics system, wherein a number of "daughter plates" are produced from so-called "mother plates", that is to say containers suitable for mechanical handling, for example a deep well plate (DWP) or, depending upon the amount of substance, a microtitre plate (MTP), which generally contain more than one dose of a substance concentrate in their wells.

For the production of a daughter plate, the amount of concentrate (active substance dissolved in an organic solvent, e.g. DMSO) required to prepare a single dose of spray mixture is taken from a well in the mother plate and introduced into the corresponding well in the daughter plate. In principle, therefore, the daughter plates correspond to the mother plate except that the wells of the daughter plate contain precisely the amount required to prepare a dose of the spray mixture (that is to say the substance to be tested), whereas the corresponding wells in the mother plate each contain a multiple of that amount.

While being transported to the testing system by the logistics system, if desired the daughter plates containing the substance concentrates are cooled, for example using $CO_2$ snow, so that the concentrates are solid in order that contamination of neighbouring wells is avoided. Furthermore, the wells in the daughter plate containing the substance concentrates will usually be closed to avoid contamination. A conventional method of closure is sealing with a cover film, which can, if desired, be adhesively bonded, heat-bonded or ultrasound-bonded to the daughter plate, or with a so-called "cap-mat", a covering provided with a large number of individual stoppers (for closing-the wells). In a Step 7, the individual substance concentrates in the wells are rendered accessible. This can be effected, for example, either by removing the cap-mat or the cover film or by leaving the cover film in place and piercing it only later in the core zone K using a pipetting needle, in which case care must be taken to ensure that there is no contamination.

In Step 7, the daughter plate containing the substance concentrates not only is opened but is also conveyed to the second input storage means 8. The purpose of the second input storage means 8 is especially to ensure that there is always a sufficient number of daughter plates containing substance concentrates available so that operation in the core zone K is continuous and the testing system is therefore utilised efficiently. It also means that, for example, in the evening daughter plates containing substance concentrates are conveyed to the second input storage means 8 in sufficient numbers for operation in the core zone K of the testing system to take place fully automatically overnight and without supervision. The individual daughter plates containing the substance concentrates are each provided with a machine-readable code (bar-code). The bar-code may again represent a serial number. Information is then stored in the data bank which indicates which substance concentrate (or which substance concentrates) is (are) present in the daughter plate having which serial number.

While the substance concentrates (active substances dissolved in solvents) are placed in readiness in daughter plates by the logistics system, in the embodiment of the testing system described here the preparation of the spray mixture containing the substance to be tested takes place within the core zone K. The provision of the individual formulation auxiliaries required for the spray mixture is not carried out within the core zone K, however, but is carried out in a Step 9. The same applies to the mixing of the formulation auxiliaries to prepare the spray mixture, which takes place in a Step 10. Finally, the finished spray mixture is made ready in a Step 11, so that within the core zone K the finished spray mixture can then be accessed automatically.

In the core zone K the testing system operates as follows: if the carrier plates carrying the leaf roundels or plants are to be used in the order in which they have been conveyed to the first input storage means 5 (first-in first-out) there will be no selection of a specific carrier plate from the whole stock of carrier plates stored temporarily in the first input storage means 5. If, however, it is desired to use a carrier plate carrying a specific type of test specimens, first of all the appropriate carrier plate is selected from the stock of carrier plates in the first input storage means 5. The carrier plate can be located by reading the bar-codes provided on the carrier plates and in this way finding the carrier plate in question by means of the information stored in the data bank ("stock control"). The bar-code on the carrier plate that is used is then read off in a Step BC1 and supplied to a memory unit 12.

The daughter plates carrying the substance-containing spray mixtures are selected in the same manner, unless they are to be used in the order in which they have been conveyed to the second input storage means 8 (first-in first-out). Then, in a Step BC2, the bar-code of the daughter plate used is read off and supplied to the memory unit 12.

As has already been explained above, however, in normal cases the substance concentrates will be not be sprayed directly onto the leaf roundels but first of all a spray mixture—the substance actually to be tested—will be prepared by means of the formulation auxiliaries. The required amount of formulation auxiliary is in that case introduced by pipette into the wells of the daughter plates in a Step 13 and the spray mixtures—the substances to be tested—are thus produced. If desired, the daughter plates are also shaken in order to achieve thorough mixing of the spray mixtures in the respective wells. The mixing can be effected in various ways, for example using a high frequency shaking device, by means of an ultrasound device or with the aid of a vortexing device (vortexer).

When the preparation of the spray mixture in Step 13 is complete, the spray mixture must then be conveyed to the spraying device. This is effected in a Step 14 in which, for example, a pipetting robot takes the spray mixtures out of the individual wells and conveys them to the spraying device, where it deposits them, for example, in a nozzle body of the spraying device. This is effected in a Step 15. The manner in which this can be effected is described in detail hereinbelow. Then, in a Step 16, the spray mixtures are sprayed onto the leaf roundels or plants in the wells.

The carrier plates in the wells of which the sprayed leaf roundels or plants are located (the carrier plates carrying sprayed leaf roundels being referred to as "test plates") are then conveyed in a Step 17 to a first output storage means 18, where the sprayed leaf roundels are able to dry, the drying being assisted, if necessary, by ventilation. If necessary or desired, before the test plate carrying the sprayed leaf roundels is conveyed to the first output storage means 18, the test plate or at least the individual wells can be sealed. The daughter plates having the empty wells are conveyed to a second output storage means 19.

In the embodiment described here, the steps which then follow are not carried out in the core zone K of the testing system. These are, on the one hand, the disposal/return or further treatment of the daughter plates, which takes place in a Step 100, and, on the other hand, the further treatment of the test plates. In a Step 101 the test plates are removed from the output storage means and, where the test substances are insecticides or fungicides, are, for example, provided with insects or contaminated with fungus spores in a Step 102 (alternatively the leaf roundels may already have been provided with insects or contaminated with fungus spores prior to being sprayed with the spray mixture, that is to say prior to being sprayed with the substance to be tested). The test plates carrying the infested leaf roundels then undergo incubation 103 and after a predetermined period of time has elapsed evaluation 104 is carried out and, if necessary, further amounts of substance concentrations are ordered in a Step 105 in order that results already obtained can be corroborated.

Individual steps and devices, some of which are carried out or are arranged in the peripheral zone P and some of which are carried out or are arranged in the core zone K, will be described in detail below with reference to embodiments.

FIGS. 2 to 5 show a portion of an embodiment of the stamping device 2, the individual parts of the stamping device being shown in different operating positions. The stamping device 2 comprises a support plate 20 having an opening 200, which is in this instance circular. The stamping device also comprises a holding-down device 21 which has in its interior a cylindrical guide 210. Arranged in the guide 210 is an annular blade 211 which is displaceable in the longitudinal direction of the cylindrical guide 210. In the interior of the annular blade 211 there is arranged an ejector 212 which is (axially) displaceable in the longitudinal direction of the blade 211. The ejector 212 itself has, passing through it, a pressure/suction channel 213, which is connected at its end 214 remote from the support plate 20 to a source of elevated pressure or reduced pressure (not shown).

FIG. 2 shows the stamping device 2 in an operating state shortly before the start of the stamping operation. The test specimen to be stamped, for example a leaf B, has already been placed onto the support plate 20 and is held in place by the holding-down device 21. Below the opening 200 is a well 300 of a microtitre plate 30 (carrier-plate) which in accordance with Step 3 (FIG. 1) already contains a nutrient solution 301.

FIG. 3 shows the stamping device 2 during the cutting operation. The blade 211 is in contact with the leaf B and the ejector 212 also. The suction channel 213 is under reduced pressure, so that the leaf roundel, once cut, cannot fall through the opening 200 into the well 300 but can later be deposited therein in a well defined manner.

FIG. 4 shows a stamping device with a stamped-out section of a leaf, that is to say with the leaf roundel BR, shortly before the leaf roundel is deposited onto the nutrient solution 301 (or the gel) located in the well 300 of the carrier plate 30. The leaf roundel BR is held in place against the ejector 212 by the reduced pressure in the suction channel 213.

FIG. 5 finally shows the stamping device during the deposition of the leaf roundel BR onto the nutrient solution 301 (or the gel), the suction channel 213 being connected to a source of elevated pressure in order to produce a slightly elevated pressure in the suction channel 213, since this facilitates the detachment of the leaf roundel BR from the ejector 212. After deposition the stamping device is brought into the starting position again so that the next leaf B can be placed onto the support plate 20 or the leaf B just stamped on the support plate 20 can be displaced in order that the next leaf roundels can be stamped out. For that purpose, of course, the opening 200 in the support plate is brought into line with the next well in the carrier plate. The stamping operation can then be carried out again and in this way the entire carrier plate 30 can be charged.

FIG. 6 shows a portion of an embodiment of the spraying device in accordance with Step 15 in FIG. 1. In this view a nozzle 151 of a nozzle body 150 has already been inserted into the well 300 in the carrier plate 30 in which the leaf roundel BR is located on the nutrient solution 301. The well 300 has been sealed by means of a sealing ring 152, so that neighbouring wells in the carrier plate are not contaminated when the leaf roundel is being sprayed with the substance to be tested through the spray channel 153 of the nozzle 151.

The substance to be tested—the spray mixture—is generally applied to the leaf roundel in the form of a spray mist A (aerosol). Since spray mist will often remain behind in the well 300 after spraying and that spray mist could subsequently contaminate leaf roundels deposited in neighbouring wells, the nozzle body 150 is also provided with an air inlet channel 154 and an air outlet channel 155. After the application, residues of spray mist that still remain behind are flushed out of the well 300 and conveyed away by feeding in fresh air and removing spray mixture aerosol, this being effected before the nozzle body 150 is lifted away from the carrier plate 30. As a result, contamination of leaf roundels deposited in neighbouring wells is reliably avoided.

FIG. 7 shows a portion of the nozzle body 150 in detail. It will be seen especially that the finished spray mixture—the substance to be tested (typically an amount of about from 10 to 100 microliters)—that has been taken out of a well in a daughter plate is introduced by pipette into a reservoir 156 using a pipetting needle PN. The reservoir 156 is connected to the spray channel 153 by way of a feed channel 157 of very small diameter. That diameter is so small that the spray mixture will not pass into the spray channel 153 unless subjected to suction. The application of suction to the spray mixture is effected by providing the end of the spray channel 153 remote from the leaf roundel with a compressed air connection. As soon as compressed air flows through the spray channel 153, reduced pressure is generated in the feed channel 157 in accordance with the Venturi principle and that reduced pressure causes the spray mixture to be sucked out of the reservoir 156 and, by way of the feed channel 157, mixed with the air flow in the spray channel 153, thus producing the mixture of substance to be tested and air which is sprayed onto the leaf roundel in the form of aerosol A. The nozzle 151 can be constructed in the form of a full-circle conical nozzle in order to achieve homogeneous spraying of the leaf roundel.

The nozzle body can also be constructed in such a manner that the reservoir (156) with the feed channel (157) is mounted perpendicularly above the nozzle (151) and the compressed air is supplied from the side by way of the spray channel (153).

The compressed air can be supplied either continuously or discontinuously (i.e. supplied only immediately before the application of the spray mixture). Continuous supply of compressed air is preferred.

Other means of applying the spray mixture—which contains the substance to be tested—to the leaf roundel are shown in FIG. 8. Those means are essentially micropipettes 158 which, with the aid of piezoelectric transducers, produce extremely fine droplets, the size of which can be controlled very accurately and which can be sprayed onto the leaf roundel with extra-ordinary accuracy. The mode of operation of such micropipettes is similar to the manner in which ink is discharged in ink-jet printers. Using the micropipette 158 shown in FIG. 8, the spray mixture can first of all be sucked out of the well in the daughter plate and into the stock container 160 by the application of reduced pressure at the pressure/suction connection 159 (which is provided with a bayonet closure). The micropipette is then lowered into the well in the carrier plate in which the leaf roundel to be sprayed is located. Using a piezoelectric droplet generator 161 (which produces an appropriate ultrasound pulse when an electrical control voltage is applied) droplets of a well defined size are then expelled from a nozzle 162 at a well defined rate. When such micropipettes are used it is unnecessary to generate a spray mixture aerosol, since by means of such micropipettes it is possible to generate droplets of sufficiently small size and, furthermore, the droplets can also be discharged with a very high degree of accuracy, so that using such pipettes the optimum droplet size for a specific substance (spray mixture) can be established. The nozzle body 150 can therefore also include such micropipettes as a variant of the embodiment according to FIG. 7. Such micropipettes and the associated system components (actuating unit) are available under the name "Autodrop-System" from Microdrop GmbH of Norderstedt (Federal Republic of Germany).

A further suitable means of applying the spray mixture to the test specimen is an ultrasound liquid atomiser which operates with a piezo-ceramics disc bonded to a metal cone, which is excited to high frequency oscillations in the kHt range (for example 100 kHz). Such means are commercially available.

If desired, it is also possible to use as means for applying the spray mixture to the test specimen a commercially available pump atomiser, as used, for example, for perfume bottles in the cosmetics industry. Pump atomisers are suitable especially for test specimens in the form of leaf roundels or comminuted parts of plants.

FIG. 9 finally is an embodiment of a nozzle body 150 in which the individual nozzles (the same applies to the micropipettes) are arranged in one or more lines. In this arrangement, the distance D between the individual nozzles corresponds to the distance E between the wells 300 of the carrier plate 30 (e.g. having twenty four or ninety six wells) in which the leaf roundels are located. In the embodiment in FIG. 9 two lines of nozzles, each having eight nozzles per line, are provided on the nozzle body 150. In this embodiment, groups of four nozzles (see cut-away view of the nozzle body at the right-hand edge of the nozzle body) are each assigned a respective reservoir 156 (i.e. there are four feed channels from this reservoir to the respective spray channels) and a compressed air connection (ie. there are four connections from this compressed air connection to the spray channels). At regular intervals, the nozzle body is moved over the carrier plate 30 and lowered, spray mixture is applied to the leaf roundels in the wells of two lines of the carrier plate simultaneously (the same spray mixture being applied to four leaf roundels and those four leaf rounders sprayed in the same manner being referred to also as replicas), the wells are flushed, the nozzle body is raised again, and so on.

Instead of leaf roundels being deposited in the individual wells of the carrier plate, it would also be possible for an entire leaf or a relatively large section thereof to be applied to a carrier plate not having such a large number of wells, but having, for example, only a single well of correspondingly large surface area but not very great depth, and accordingly being so constructed that the leaf or a relatively large section thereof can be placed in readiness on a nutrient solution or a gel. Especially when the above-described "Autodrop-System" of Microdrop GmbH of Norderstedt (Federal Republic of Germany) is used it is possible, as already mentioned, to effect the application of the substances to be tested with very great accuracy, so that there can be virtually no contamination provided that neighbouring points being sprayed are arranged at a suitable minimum distance apart. In that case the carrier plate having a large number of individual wells containing the individual leaf roundels is replaced by simply a carrier plate having an entire leaf or a relatively large section thereof. The individual points to which the substances to be tested are then applied must simply be far enough apart to ensure that, with very accurate application of the substances to be tested, neighbouring points cannot become contaminated, but this is very readily possible in principle.

In a preferred embodiment of the testing system according to the invention, a spraying device (150, 151, 158) is positioned immediately above the well(s) (300) of the carrier plate (30) and sprays the test specimen deposited therein with the selected substance or the selected substance mixture. In this embodiment the contamination of neighbouring test specimens by direct contact with the spray mist can be prevented by limiting the angle of the spray jet to the open diameter of a well (300), for example by means of a suitable attachment.

Such an attachment for the spraying device (150, 151, 158) advantageously has the same open cross-section as a well (300), but may also have a smaller open cross-section. The attachment can be rigidly or displaceably connected to the spraying device (150, 151, 158) or can be positioned above the wells (300) by means of a suitable holding device immediately before spraying. An attachment of that kind has, for example, the shape of a tube, the length of which is so selected that the angle of the spray jet is limited to the open cross-section of the well (300) by the walls of the tube. When the test specimen is a leaf roundel, the attachment is preferably rigidly or displaceably connected to the spraying device (150, 151, 158).

It is also possible for the attachment to be placed directly onto the carrier plate (30) before spraying. In this embodiment of the testing system according to the invention the attachment is preferably in the form of a three-dimensional grid, which corresponds in length and width to the carrier plate (30) and in which the number of meshes corresponds to the number of wells (300) on the carrier plate, the centre point of the meshes being located above the centre point of the respective wells (300), so that the wall height of the meshes forms an extension of the wall height of the wells (300). The meshes preferably have the same open aperture as the wells (300).

The use of a three-dimensional grid is especially advantageous when the test specimen is a plant, especially a plant that, by the time of application of the substance or substance mixtures, has already grown above the rim of the carrier plate (30). In this embodiment, the three-dimensional grid is placed onto the carrier plate (30) before the emergence of the plants. As a result, the walls of the wells (300) are raised in such a manner that a plant emerging above the rim of the carrier plate (30) cannot be contaminated by the spraying of a neighbouring plant. The three-dimensional grid can also be formed in such a manner that two or more similar grids can be stacked one above the other in order that the total wall height of the meshes can be matched as desired to the expected growing height of the plant variety in question.

The testing system described with reference to the Figures enables a very large number of substances and test specimens to be tested and allows reliable identification and categorisation of the test specimens and of the tested substances. Furthermore, contamination of neighbouring test specimens (leaf roundels) is reliably avoided and therefore the result of the test is not affected or falsified. Furthermore, the testing system according to the invention allows fully automatic operation to a greater or lesser extent, especially overnight and without supervision. A particular advantage of the testing system according to the invention is that even extremely small amounts of spray mixture (10 to 100 microliters) can be sprayed in finely divided form onto the plants or parts of plants with a high degree of accuracy.

What is claimed is:

1. A testing system for testing substances for their pesticide activity comprising
   a) a memory unit (12) for storage of a test specimen and a test substance by means of a machine-readable code,
   b) a carrier plate (30) wherein the test specimens being placed in readiness by deposition of each test specimen or a section (BR) thereof in a well (300) that is provided in the carrier plate (30) and is at least partly filled with a nutrient solution (301) or a gel, and
   c) a spraying device (150, 151, 158) which positions immediately above the well(s) (300) of the carrier plate (30) and sprays the test specimen deposited therein with the selected test substance, or inserts into the well(s) (300) of the carrier plate (30) and sprays the test specimen deposited therein with the selected test substance and then reemerges from the well (300).

2. A testing system according to claim 1, having a first inlet storage means (5) in which a large number of carrier plates (30) charged with test specimens is stored temporarily before spraying.

3. A testing system according to claim 1, wherein the spraying device comprises a nozzle body (150) having a sealing ring (152) which is so arranged that, on insertion of the nozzle(s) (151) of the nozzle body (150) into the respective well (300) of the carrier plate (30), the sealing ring tightly surrounds the well (300) in the carrier plate (30), and the spraying device has a reservoir (156) for the substance to be applied to the test specimen or the substance mixture to be applied to the test specimen and a spray channel (153) which is provided with a compressed air connection at its end remote from the test specimen, the reservoir (156) and the spray channel (153) being connected to one another by a very narrow feed channel (157) which opens into the spray channel (153).

4. A testing system according to claim 1, wherein the spraying device comprises one or more micropipettes (158), each of which has a stock container (160) into which the test substance or the test substance mixture is first introduced by suction, and then, using a piezoelectric droplet generator, one or more droplets of a well defined size are expelled through a nozzle (162) at a well defined rate and the test specimen is thus sprayed.

5. A testing system according to claim 1, wherein the nozzle body (150) has a plurality of linearly arranged nozzles and associated reservoirs and also spray and feed channels and sealing rings or a plurality of linearly arranged micropipettes (158), the distance (D) between the individual nozzles or micropipettes corresponding to the distance (E) between the wells (300) within a line of the carrier plate (30).

6. A testing system according to claim 1, wherein the nozzle body (150) comprises an air inlet channel (154) or channels and an air outlet channel (155) or channels, which are each so arranged that while the nozzle (151) is inserted in the respective well (300) in the carrier plate (30) the channels are in communication with the well (300).

7. A testing system according to claim 1, wherein the test substances are tested for insecticidal, fungicidal, herbicidal, acaricidal or nematicidal activity.

* * * * *